US012102974B2

United States Patent
Piepiora et al.

(10) Patent No.: US 12,102,974 B2
(45) Date of Patent: Oct. 1, 2024

(54) REACTOR FOR THE CONVERSION OF CARBON DIOXIDE

(71) Applicants: Paris Sciences et Lettres, Paris (FR); Centre National de la Recherche Scientifique (CNRS), Paris (FR); Sorbonne Universite, Paris (FR); Ecole Nationale Superieure de Chimie de Paris, Paris (FR); Univ Paris XIII Paris-Nord Villetaneuse, Villetaneuse (FR)

(72) Inventors: Vincent Piepiora, Versailles (FR); Stéphanie Ognier, Paris (FR); Simeon Cavadias, Rueil Malmaison (FR); Xavier Duten, Fontenay-sous-Bois (FR); Michael Tatoulian, Paris (FR); Maria Elena Galvez-Parruca, Pantin (FR); Patrick Da Costa, Pantin (FR)

(73) Assignees: Paris Sciences et Lettres (FR); Centre National de la Recherche Scientifique (CNRS) (FR); Sorbonne Universite (FR); Ecole Nationale Superieure de Chimie de Paris (FR); Univ Paris XIII Paris-Nord Villetaneuse (FR)

( * ) Notice: Subject to any disclaimer, the term of this patent is extended or adjusted under 35 U.S.C. 154(b) by 660 days.

(21) Appl. No.: 17/416,225

(22) PCT Filed: Dec. 20, 2019

(86) PCT No.: PCT/EP2019/086743
§ 371 (c)(1),
(2) Date: Jun. 18, 2021

(87) PCT Pub. No.: WO2020/128009
PCT Pub. Date: Jun. 25, 2020

(65) Prior Publication Data
US 2022/0040664 A1    Feb. 10, 2022

(30) Foreign Application Priority Data

Dec. 21, 2018  (FR) .................................... 1874033

(51) Int. Cl.
*B01J 19/08*    (2006.01)
*B01J 8/06*     (2006.01)
(Continued)

(52) U.S. Cl.
CPC ............... *B01J 19/088* (2013.01); *B01J 8/06* (2013.01); *B01J 19/242* (2013.01); *B01J 23/755* (2013.01);
(Continued)

(58) Field of Classification Search
CPC .............. B01J 19/088; B01J 2219/0809; B01J 2219/0815; B01J 2219/0828;
(Continued)

(56) References Cited

U.S. PATENT DOCUMENTS

| 5,843,383 A | 12/1998 | Williamson et al. |
| 2005/0106085 A1 | 5/2005 | Calvo et al. |

(Continued)

FOREIGN PATENT DOCUMENTS

| CN | 1360008 A | 7/2002 |
| EP | 1052220 A2 | 11/2000 |

(Continued)

OTHER PUBLICATIONS

E&E Consultant., titled "Etude portant sur l'hydrogène et la méthanation comme procédé de valorisation de l'électricité excédentaire", Sep. 2014, 238 pages (Executive summary in English is present from p. 19 to p. 27).

(Continued)

*Primary Examiner* — Lessanework Seifu
(74) *Attorney, Agent, or Firm* — Lerner David LLP

(57) ABSTRACT

The present invention concerns a reactor for the conversion of carbon dioxide or carbon monoxide into hydrocarbon (Continued)

and/or alcohol comprising a support made from an electrically and thermally conductive material, forming the wall or walls of at least one longitudinal channel that passes through the support and also acting as the cathode of the reactor, at least one wire electrode forming an anode of the reactor, and extending within each longitudinal channel, and being arranged at a distance from the wall or walls of the longitudinal channel, each wire electrode optionally being covered with an electrically insulating layer along the part of the wire electrode extending within the longitudinal channel, a catalyst capable of catalysing a conversion reaction for the conversion of carbon dioxide or carbon monoxide into hydrocarbon and/or alcohol, the catalyst being situated between the wire electrode and the wall or walls of each longitudinal channel.

19 Claims, 11 Drawing Sheets

(51) Int. Cl.

| | | |
|---|---|---|
| *B01J 19/24* | (2006.01) | |
| *B01J 23/755* | (2006.01) | |
| *C07C 1/04* | (2006.01) | |
| *C07C 1/12* | (2006.01) | |
| *C07C 29/152* | (2006.01) | |
| *C07C 29/156* | (2006.01) | |
| *H05H 1/24* | (2006.01) | |

(52) U.S. Cl.
CPC ................ *C07C 1/041* (2013.01); *C07C 1/12* (2013.01); *C07C 29/152* (2013.01); *C07C 29/156* (2013.01); *H05H 1/2406* (2013.01); *H05H 1/2431* (2021.05); *H05H 1/245* (2021.05); *B01J 2219/0809* (2013.01); *B01J 2219/0815* (2013.01); *B01J 2219/0828* (2013.01); *B01J 2219/083* (2013.01); *B01J 2219/0841* (2013.01); *B01J 2219/0849* (2013.01); *B01J 2219/0871* (2013.01); *B01J 2219/0875* (2013.01); *B01J 2219/0892* (2013.01); *B01J 2219/0896* (2013.01); *B01J 2219/182* (2013.01); *B01J 2219/1943* (2013.01); *B01J 2219/2408* (2013.01); *B01J 2219/2411* (2013.01); *B01J 2219/243* (2013.01); *C07C 2523/755* (2013.01); *H05H 2245/15* (2021.05)

(58) Field of Classification Search
CPC .......... B01J 2219/083; B01J 2219/0841; B01J 2219/0849; B01J 2219/0871; B01J 2219/0875; B01J 2219/0892; B01J 2219/0896; B01J 2219/182; B01J 2219/1943; B01J 2219/2408; B01J 2219/2411; B01J 2219/243; B01J 2219/0898

See application file for complete search history.

(56) References Cited

U.S. PATENT DOCUMENTS

| | | | |
|---|---|---|---|
| 2014/0284206 | A1 | 9/2014 | Guo et al. |
| 2017/0355919 | A1 | 12/2017 | Kim et al. |
| 2022/0070993 | A1* | 3/2022 | Ha .................... H05H 1/245 |

FOREIGN PATENT DOCUMENTS

| | | | |
|---|---|---|---|
| EP | 3050865 | A1 | 8/2016 |
| FR | 2836397 | A1 | 8/2003 |
| WO | 0049278 | A1 | 8/2000 |
| WO | 0154806 | A1 | 8/2001 |

OTHER PUBLICATIONS

French Search Report for Application No. FR 1874033, dated Sep. 17, 2019, 9 pages.
Gao Et Al., titled "A thermodynamic analysis of methanation reactions of carbon oxides for the production of synthetic natural gas", RSC Advances, Year 2012, 2, 2358-2368.
Hoeben, Et Al., Titled "Plasma driven, water assisted CO2 methanation", Year 2015, pp. 1-6.
International Search Report for Application No. PCT/EP2019/086743, dated Jan. 29, 2020, 3 pages.
Ocampo Et Al., Applied Catalysis A: General., Titled "Methanation of carbon dioxide over nickel-based Ce0.72Zr0.28O2 mixed oxide catalysts prepared by sol-gel method", year 2009, pp. 90-96.

* cited by examiner

REACTOR FOR THE CONVERSION OF CARBON DIOXIDE

CROSS-REFERENCE TO RELATED APPLICATIONS

The present application is a national phase entry under 35 U.S.C § 371 of International Application No. PCT/EP2019/086743 filed Dec. 20, 2019, which claims priority from French Application No. 1874033 filed Dec. 21, 2018, all of which are hereby incorporated herein by reference.

FIELD OF THE INVENTION

The present invention applies to the field of conversion of carbon dioxide and/or carbon monoxide and refers more particularly to a reactor for conversion of carbon dioxide and/or carbon monoxide into hydrocarbon and/or alcohol, as well as a process for conversion of carbon dioxide and/or carbon monoxide using such a reactor.

PRIOR ART

Carbon dioxide is produced in large quantities industrially, often in the form of discharge. There is an increasing need to lower carbon dioxide emissions. For this purpose, it is possible to convert carbon dioxide into a recoverable element such as hydrocarbon and/or alcohol.

Gao et al. [1] describe a fixed-bed catalytic reactor used for converting carbon dioxide into hydrocarbon. The catalyst of such a reactor must be utilised at a temperature of around 350° C. and at a pressure greater than 20 bars for converting carbon dioxide. The catalyst is deposited onto the surface of a support (for example a metallic grille or a silicon element) forming a fixed structure. Reactive gases circulate in the reactor above the fixed structure and react to the surface of the latter with the catalyst. The reaction is temperature-controlled by flow of a heat transfer fluid in contact with the reactor. However, this type of reactor requires the installation of much equipment so as to satisfy the pressure and temperature conditions required for conversion of carbon dioxide. Implementing this equipment generates high production costs of the device comprising the reactor [2].

To this end, Ocampo et al. [3] describe the conversion of $CO/CO_2$ into methane by using a fixed-bed catalytic reactor at atmospheric pressure. But conversion of CO into carbon graphite causes a drop in yield of over 50% after 150 h of use.

Hoeben et al. [4] describe a reactor enabling methanation of carbon monoxide and potentially carbon dioxide at ambient temperature. The reactor comprises an electrode made of NiCr alloy and a water bed. High-voltage discharges are transmitted to the electrode to generate plasma in the reactor. This document also specifies that it is possible to hydrogenate carbon monoxide, and potentially carbon dioxide, without using a catalyst for the reaction.

However, this reactor detects only traces of the methanation of $CO_2$, but fails to convert $CO_2$ at rates sufficient for industrial application. This document points out in particular that improvement of the $CO_2$ methanation rate could be obtained by using a Nickel-based catalyst with low-temperature plasma, by using pulsed discharges of corona type having a rise time of under a nanosecond and by adjusting the spatial and energetic distribution of the plasma.

PRESENTATION OF THE INVENTION

An aim of the invention is to propose a solution for converting carbon dioxide and/or carbon monoxide into hydrocarbon and/or alcohol at atmospheric pressure and at low temperature. Another aim of the invention is to propose a solution for converting carbon dioxide and/or carbon monoxide with a rate higher than the rates described in the prior art. Another aim of the invention is to propose a reactor structure for conversion of carbon monoxide and/or carbon dioxide adapted to said higher rate.

Therefore, the present invention relates to a reactor for conversion of carbon dioxide and/or carbon monoxide into hydrocarbon and/or alcohol comprising:
- a support made of electrically and thermally conductive material, said support forming the wall or walls of at least one longitudinal channel which passes through the support and also acts as cathode of the reactor,
- at least one wire electrode forming an anode of the reactor, each wire electrode extending within each longitudinal channel, along said longitudinal channel, and being arranged at a distance from the wall or walls of said longitudinal channel, each wire electrode being optionally covered by an electrically insulating layer along the part of the wire electrode extending within said longitudinal channel,
- a catalyst adapted to catalyse a conversion reaction of carbon dioxide or carbon monoxide into hydrocarbon and/or alcohol, the catalyst being located between the wire electrode and the wall or walls of each longitudinal channel.

The invention is advantageously completed by the following characteristics, taken individually or in any of their possible technical combinations:
- the longitudinal channel is a cylinder of revolution, and the wire electrode is positioned along the axis of revolution of the cylinder of revolution,
- each longitudinal channel is fitted with two stoppers made of electrically insulating material positioned respectively at each of the ends of said longitudinal channel, each stopper being permeable to gas and having a through passage into which the wire electrode is inserted,
- the support is made of metal, especially steel and preferably stainless steel,
- the longitudinal channel has a diameter of less than 2 cm, especially less than 1 cm, and the length of the channel is less than 20 cm, especially less than 10 cm and preferably less than 5 cm,
- the catalyst comprises at least one element selected from cerium dioxide, such as mesoporous cerium dioxide, nickel, zirconium dioxide, hydrotalcite, clay and their mixtures,
- the support also forms a flow channel of a heat transfer fluid, and at least one obstacle, preferably a pillar, in the flow channel of the heat transfer fluid, each obstacle comprising a single longitudinal channel, the flow channel of the heat transfer fluid and said longitudinal channel being separated by the support,
- the reactor comprises a bidimensional network of longitudinal channels according to a plane of the network, preferably a hexagonal network of longitudinal channels, the longitudinal channels being parallel to each other and perpendicular to the plane of the network,
- the network has a mesh defining a mesh surface, and the form of the support is adapted so that the average speed of the heat transfer fluid in flow measured on a mesh surface in a plane parallel to the plane of the network and centred on an axis of revolution of a first cylinder is between 0.5 and 1.5 times the average speed of the heat transfer fluid on a mesh surface in a plane parallel to the plane of the network and centred on an axis of revolution of a second cylinder adjacent to the first cylinder.

Another object of the invention is a device for conversion of carbon dioxide and/or carbon monoxide into hydrocarbon and/or alcohol, comprising a conduit having a main flow axis, the conduit comprising at least one reactor according to at least one embodiment of the invention, preferably a plurality of reactors according to at least one embodiment of the invention, positioned along at least one part of the conduit, each support of each reactor extending mainly according to at least one part of a section normal to the main flow axis of the conduit, the support being formed and positioned in the conduit such that the longitudinal channels are parallel to the main flow axis of the conduit.

Advantageously, the conduit has a fluid input and a fluid output, and also comprises:
- a gas diffuser comprising carbon dioxide or carbon monoxide and hydrogen, connected to the fluid input, and
- at least one condenser, connected to the fluid output and adapted to condense at least one element from water and a hydrocarbon.

Another object of the invention is a process for conversion of carbon dioxide and/or carbon monoxide, comprising the steps of:
(a) providing a reactor according to an embodiment of the invention,
(b) injection of a gas comprising carbon dioxide and/or carbon monoxide, and dihydrogen into the longitudinal channel or longitudinal channels of the reactor,
(c) application of an electrical potential between the support acting as cathode and the wire electrode or electrodes acting as anode, the potential being adapted to generate plasma in the volume of the longitudinal channel or longitudinal channels in between the wire electrode and the wall or walls of each longitudinal channel.

By way of advantage, the process also comprises a step (d) for control of the temperature between 150° C. and 300° C., and preferably between 250° C. and 300° C., inside the reactor. The control step (d) of the temperature comprises for example injection of the heat transfer fluid, or looped circulation of the heat transfer fluid in the flow channel of a reactor according to an embodiment of the invention.

Advantageously, the electrical potential applied in step (c) has a frequency of between 1 MHz and 20 MHz.

DESCRIPTION OF THE FIGURES

Other characteristics, aims and advantages of the invention will emerge from the following description which is purely illustrative and non-limiting and which must be considered with respect to the appended drawings, in which.

DEFINITION

In the present invention the term "diameter" of a longitudinal channel designates the maximal dimension of a normal section of said longitudinal channel.

In the present invention the term "hydrocarbon" designates a saturated or unsaturated hydrocarbon molecule, linear or branched, or a mixture of such molecules. Preferably, this is methane.

In the present invention the term "alcohol" designates a molecule of formula R—OH where R represents a saturated or unsaturated hydrocarbon chain, linear or branched, or a mixture of such molecules. Preferably, this is methanol.

In the present invention the term "heat transfer fluid" designates a fluid adapted to transporting heat between two temperature sources. This can be oil, air, and/or an aqueous solution, and preferably oil.

DETAILED DESCRIPTION OF THE INVENTION

Architecture of the Reactor 1

The reactor 1 is adapted to convert carbon dioxide and/or carbon monoxide into a hydrocarbon and/or an alcohol by generating plasma in the reactor 1.

Figure 1:
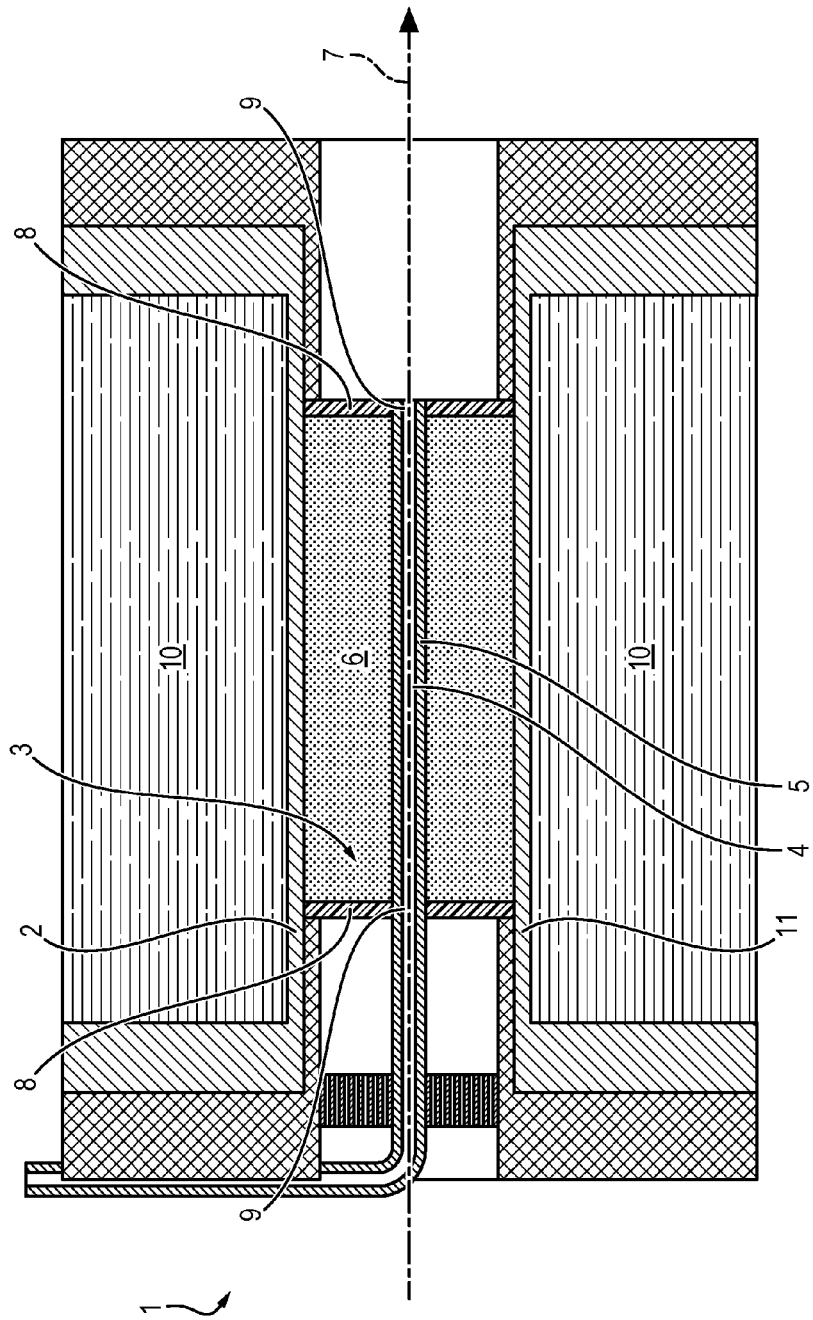
FIG. 1 schematically illustrates a part of a reactor according to an embodiment of the invention comprising a longitudinal channel, FIG. 2 schematically illustrates a part of a reactor according to an embodiment of the invention comprising a wire electrode and two stoppers, FIG. 3 schematically illustrates a part of a reactor according to an embodiment of the invention, comprising a wire electrode and two stoppers, FIG. 4 schematically illustrates a part of a device according to an embodiment of the invention comprising a reactor, FIG. 5 schematically illustrates a section through a reactor according to an embodiment of the invention comprising a network of longitudinal channels, FIG. 6 schematically illustrates a reactor according to an embodiment of the invention comprising a network of longitudinal channels, FIG. 7 schematically illustrates a reactor according to an embodiment of the invention comprising a network of longitudinal channels, and a flow channel of the heat transfer liquid, FIG. 8 schematically illustrates a device according to an embodiment of the invention comprising a reactor according to an embodiment of the invention, FIG. 9 schematically illustrates a device according to an embodiment of the invention comprising four reactors, FIG. 10 schematically illustrates a device according to an embodiment of the invention, FIG. 11 schematically illustrates a reactor according to an embodiment of the invention comprising a network of longitudinal channels, FIG. 12 schematically illustrates a reactor according to an embodiment of the invention comprising a network of longitudinal channels, FIG. 13 schematically illustrates a reactor according to an embodiment of the invention comprising a network of longitudinal channels.

FIG. 1 schematically illustrates a part of a reactor 1 for conversion of carbon dioxide and/or carbon monoxide into hydrocarbon and/or alcohol according to an embodiment of the invention. The reactor 1 comprises a support 2 made of electrically and thermally conductive material. The support 2 is preferably made of metal, especially steel, and preferably stainless steel. Therefore, the performances of the support 2 at the same time thermal, electrical and mechanical are maximised. The support 2 forms the wall or walls of at least one longitudinal channel 3. The longitudinal channel 3 passes through the support 2. The longitudinal channel 3 especially has a diameter of less than 10 cm, especially less than 5 cm, and preferably less than 2 cm. The length of the longitudinal channel 3 is preferably less than 20 cm, especially less than 10 cm, and more preferably less than 5 cm. Therefore, it is possible to apply gradients of sufficiently high electrical potentials with voltage generators of the prior art to generate plasma in the longitudinal channel 3.

The reactor 1 comprises at least one wire electrode 4 which forms an anode of the reactor 1. The wire electrode 4 is arranged at a distance from the wall or walls of the longitudinal channel 3 which form the cathode. The wire electrode 4 extends within the longitudinal channel 3. It can extend along part of the longitudinal channel 3 and preferably over the entire length of the longitudinal channel 3. Therefore, the spatial distribution of the plasma is homogeneous in the longitudinal channel 3. Preferably, the longitudinal channel 3 is a cylinder of revolution having an axis of revolution 7. The wire electrode 4 is positioned along the axis of revolution 7. Therefore, the gradient of electrical potential can be homogeneous in the volume of the longitudinal channel 3 between the cathode and the anode.

During conversion of carbon dioxide and/or carbon monoxide plasma is generated in some of the volume formed by the longitudinal channel or longitudinal channels 3, in between the wire electrode 4 and the wall or walls of each longitudinal channel 3. Plasma is generated by dielectric barrier discharge (also known by the term controlled dielectric barrier discharge, or DBD). Dielectric barrier discharge is an electrical discharge created between two electrodes separated by a dielectric material. This discharge can be pulsed for example when the selected dielectric material is a dielectric gas. In the reactor 1, the dielectric can be selected at least from a layer 5 comprising a solid dielectric material, displaced on the wire electrode 4, a layer comprising a solid dielectric material displaced on the cathode, or the gaseous phase separating the two electrodes, comprising carbon dioxide for example. Each wire electrode 4 is preferably covered by an electrically insulating layer 5 along the part of the wire electrode extending within the longitudinal channel 3. Therefore, it is possible to impose voltages in the reactor between the cathode and the anode greater than 10 kV, and preferably greater than 20 kV. The layer 5 can preferably be made of alumina.

The reactor 1 also comprises a catalyst 6 adapted to catalyse a conversion reaction of carbon dioxide and/or carbon monoxide of hydrocarbon and/or alcohol. The catalyst 6 is arranged between the wire electrode 4 and the wall or walls of each longitudinal channel 3.

The catalyst 6 preferably comprises at least one element selected from magnesium oxide, silicon oxide, lanthanum oxide, cerium oxide, zirconium oxide and aluminium oxide. The catalyst 6 comprises especially at least one element selected from magnesium oxide, lanthanum oxide, cerium dioxide and zirconium oxide and their combinations, said oxide or said oxides being impregnated by nickel or cobalt, preferably in metallic form. Oxides can originate from hydrotalcites, hydrocalumite or natural clays. The catalyst 6 can comprise a substrate comprising mesopores. The substrate can have a zeolitic structure.

The nickel content can advantageously be between 5 to 30% by mass relative to the total composition of the catalyst 6. The cobalt content can advantageously be between 5 to 30% by mass relative to the total composition of the catalyst 6. The zircon content (other name for zirconium oxide), in particular in the case of a catalyst 6 comprising a composite oxide of cerium and zircon, can be between 1% to 20% by mass relative to the total composition of the catalyst 6. The cerium oxide content can be between 5 to 30% by mass relative to the total composition of the catalyst 6. The silicon oxide content can be between 15 to 40% by mass relative to the total composition of the catalyst 6. The aluminium oxide content can be between 15 to 40% by mass relative to the total composition of the catalyst 6. The magnesium oxide content can be between 1 to 20% by mass relative to the total composition of the catalyst 6. The lanthanum oxide content can be between 1 to 10% by mass relative to the total composition of the catalyst 6.

The catalyst 6 can be activated by the electrical potential controlled between the cathode and the electrode. "Activated" means that the electrical potential forms positively or negatively polarised sites on the surface of the catalyst 6. These polarised sites favour adsorption and desorption of elements of the gaseous phase, allowing conversion of carbon dioxide and/or carbon monoxide. This catalysis is particularly advantageous as it can be carried out at temperatures below 350° C.

The longitudinal channel 3 is fitted with two stoppers 8 positioned at each of the ends of the longitudinal channel 3. Each stopper 8 is made at least of one electrically insulating material. Each stopper 8 is also permeable to gas. Finally, at least one stopper 8 positioned in a longitudinal channel 3, preferably both stoppers 8, presents a through passage 9 into which the wire electrode 4 can be inserted. The stopper 8 has several functions. It supports the wire electrode 4 on either side of the ends of the longitudinal channel 3. The stopper 8 also electrically insulates the volume defined inside the longitudinal channel 3 from the rest of the reactor 1. Therefore, the plasma generated during use of the reactor 1 is confined in the longitudinal channel or longitudinal channels. Finally, due to their permeability to gas the stoppers 8 perform the two preceding functions and allow gas flow from one end of the longitudinal channel 3 to the other so as to introduce carbon dioxide and/or carbon monoxide to the longitudinal channel 3. The stoppers 8 also release any resulting hydrocarbon and/or alcohol.

The support 2 forms a flow channel 10 of a heat transfer fluid 13. The flow channel 10 of the heat transfer fluid and the longitudinal channel 3 are separated by the support 2. As the support 2 is both electrically and thermally conductive, at the same time it plays the role of cathode of the reactor 1, enabling plasma to be generated in the longitudinal channel 3, and plays the role of heat exchanger, allowing exchange of heat between the longitudinal channel 2 and the flow channel 10. The support 2 also acts as mechanical support of the reactor 1.

Figure 2:
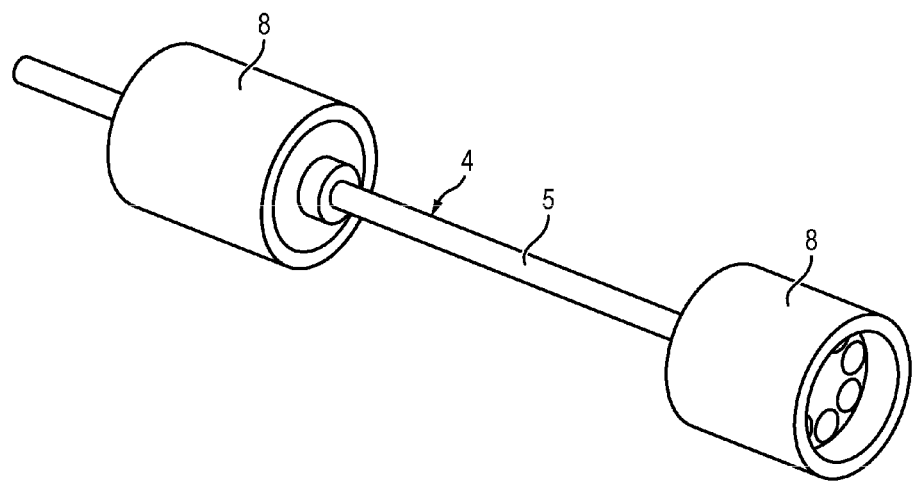

In reference to FIG. 2, the wire electrode 4 can be inserted into the two stoppers 8 of a longitudinal channel 3. A stopper 8 can for example comprise a sleeve made of ceramic, enclosing a part of the wire electrode 4 intended to be arranged at one of the ends of the longitudinal channel 3. The sleeve forms the passage 9 of the stopper. The sleeve can be enclosed by a sintered glass part. The sintered glass part itself can be enclosed by a cylindrical part made of ceramic. The cylindrical part made of ceramic can for example have openings for a gas flow to pass through the stopper 8.

Figure 3:
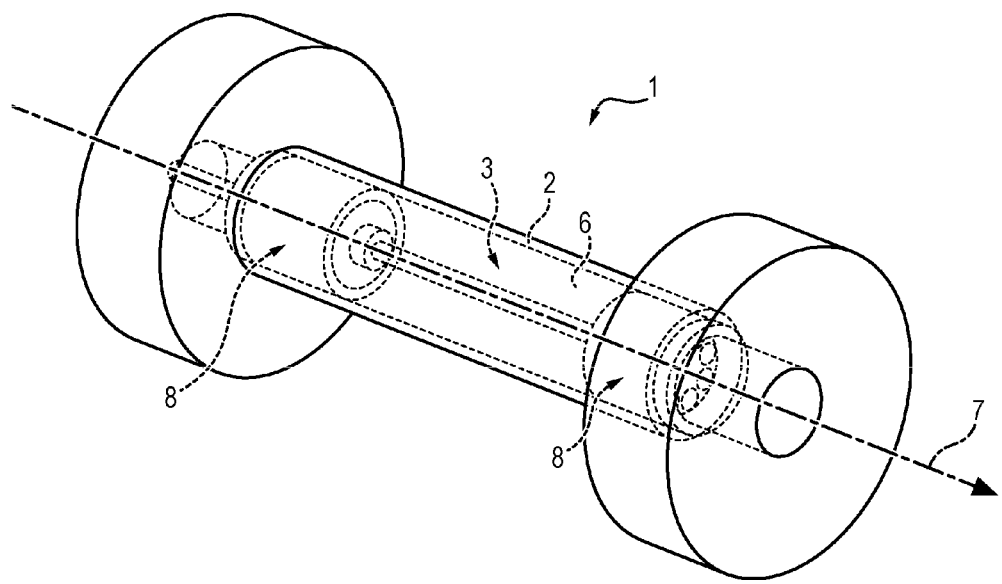

In reference to FIG. 3, a part of the support 2 can enclose each of the cylindrical parts of the stopper 8 so as to form the longitudinal cylindrical channel 3 around the axis of revolution 7.

In reference to FIG. 4, FIG. 5, FIG. 6 and FIG. 7, the support 2 can form a bidimensional network 12 of longitudinal channels 3. The bidimensional network 12 can be planar, according to a plane of the network 12. The longitudinal channels 3 can preferably be parallel to each other and perpendicular to the plane of the network 12. Therefore, the longitudinal channels 3 can be oriented so as to allow a gas flow to pass through the support 2 from one of the semi-spaces formed by the plane of the network to the other semi-space formed by the plane of the network 12. The support 2 preferably forms a plurality of longitudinal channels, specifically at least 2, especially at least 50, in particular at least 1000, and more preferably at least 2500 longitudinal channels 3. Due to the mechanical support function of the support 2 and cathode, manufacturing a reactor 1 comprising a plurality of longitudinal channels is simplified.

Figure 4:
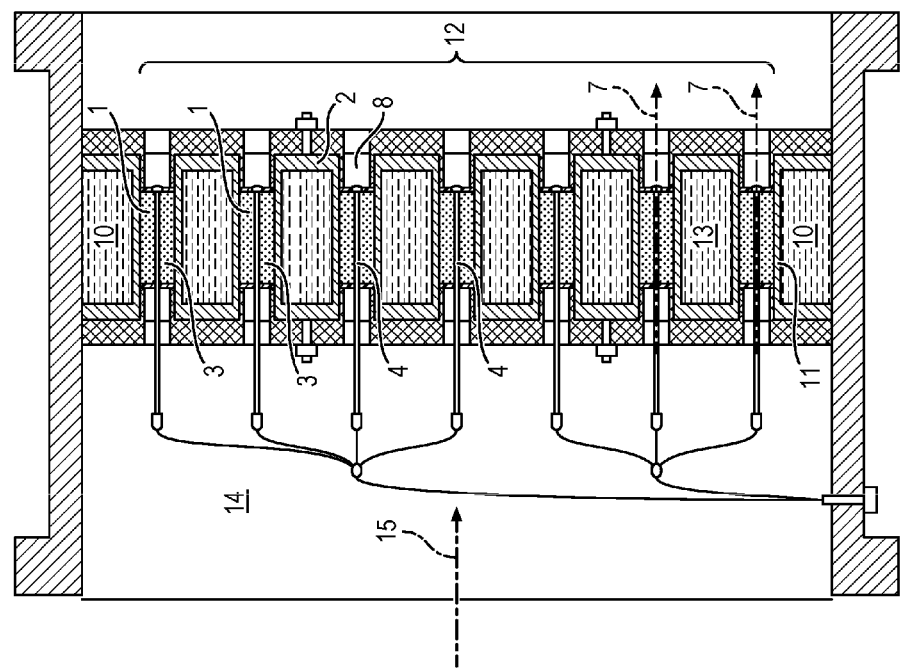

FIG. 4 schematically illustrates the section of a reactor 1 according to a plane perpendicular to the plane of the network 12. A wire electrode 4 is inserted into each of the longitudinal channels 3 formed by the support 2. Each electrode 4 can be connected electrically to the other electrodes 4 by a tree of electrically conductive wires. The root of the tree has an electrical connection, intended to be connected to the outside of the reactor 1. The other apices of the tree have electrical connections with the wire electrodes 4.

Figure 5:
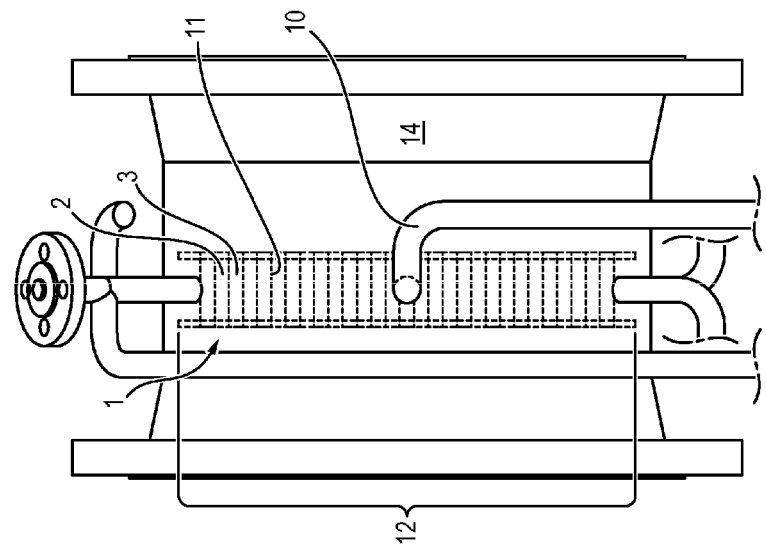

FIG. 5 schematically illustrates the reactor 1 comprising a network 12 of longitudinal channels 3 viewed from the side. The support 2 forms a flow channel 10 of the heat transfer fluid 13. FIG. 5 schematically illustrates one input and two outputs for heat transfer fluid 13, allowing flow of the heat transfer fluid 13 in the flow channel 10.

Figure 6:
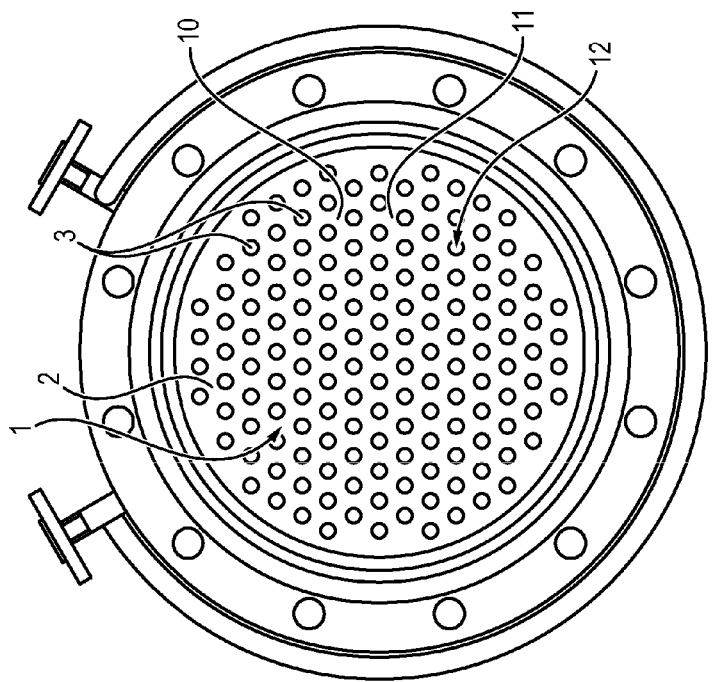

FIG. 6 schematically illustrates a frontal view of the reactor illustrated in FIG. 5. The support 2 forms a hexagonal bidimensional network 12 of longitudinal channels 3 (network of honeycomb type). At the same time the support 2 forms the flow channel 10 of the heat transfer fluid, and obstacles 11, preferably pillars, in the flow channel 10 of the heat transfer fluid 13. Each obstacle 11 comprises a single longitudinal channel 3, the flow channel 10 of the heat transfer fluid 13 and said longitudinal channel 3 being separated by the support 2.

Figure 7:
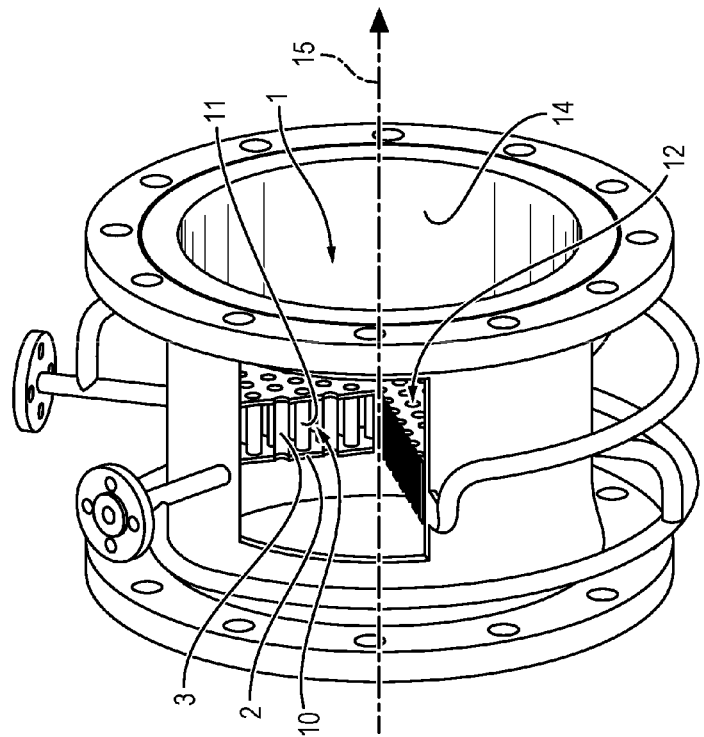

FIG. 7 schematically illustrates a perspective view of the reactor 1. In FIG. 7, the reactor 1 is cut away so as to illustrate the separation between the flow channel 10 and the longitudinal channels 3 by the support 2. The flow channel 10 allows heat transfer fluid 13 to flow around each of the obstacles 10 and therefore around each of the longitudinal channels 3 so as to regulate the temperature in each of the longitudinal channels 3.

Architecture of the Device 16

Figure 8:
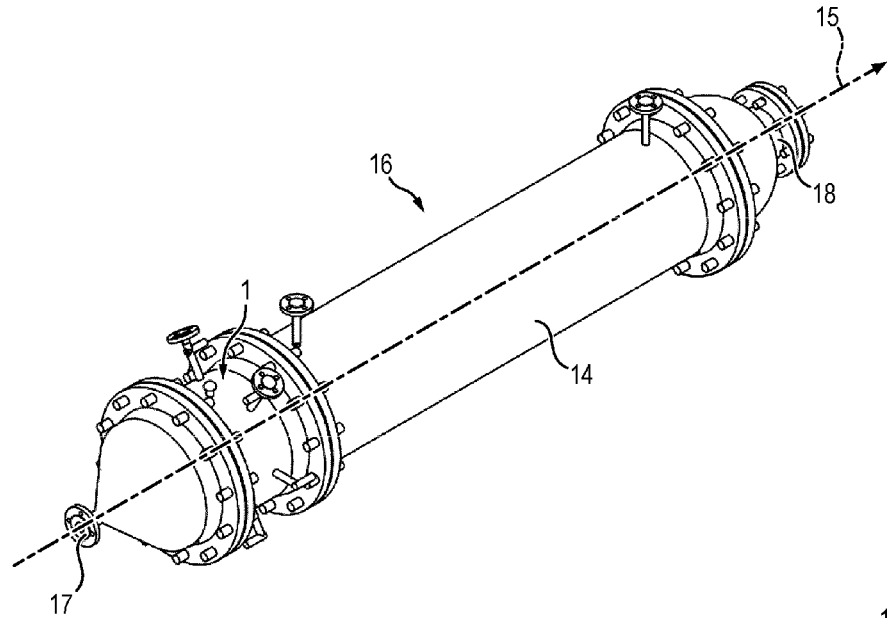
Figure 9:
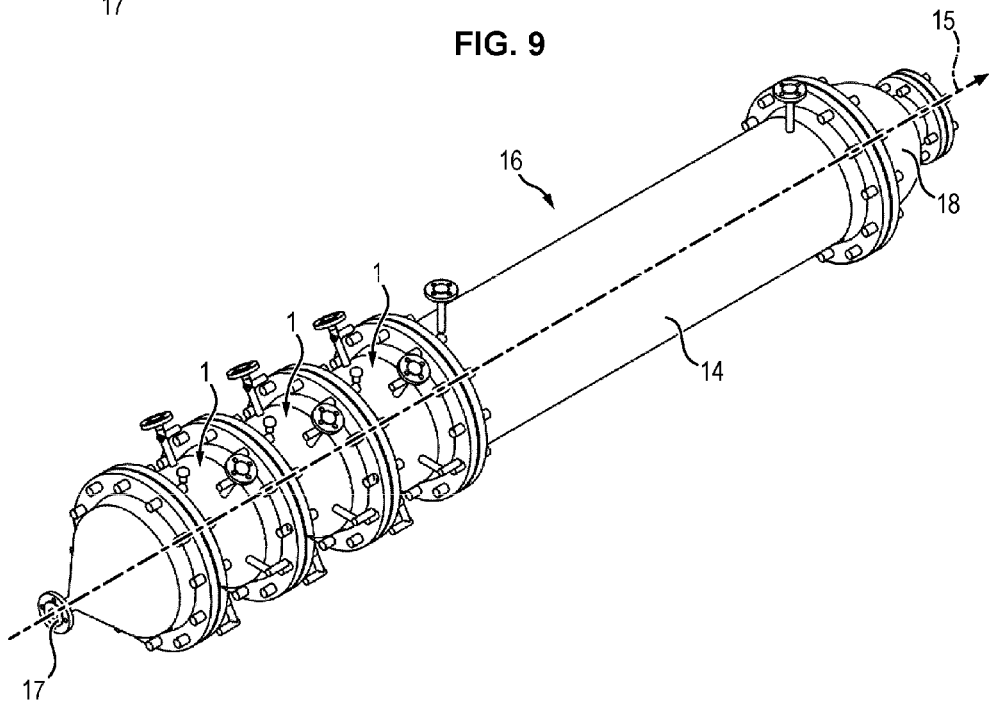

In reference to FIG. 8 and FIG. 9, another object of the invention is a device 16 comprising a conduit 14. The conduit 14 has a main flow axis 15, a fluid input 17 and a fluid output 18. The fluid input 17 can be connected to a gas source comprising carbon dioxide and/or carbon monoxide intended to be converted. The fluid input 17 can preferably be connected to a gas diffuser comprising carbon dioxide and/or carbon monoxide and dihydrogen.

The conduit 14 comprises at least one reactor 1, and preferably a plurality of reactors 1, positioned in series along the conduit 14. Each support 2 of each reactor 1 extends mainly according to at least one part of a section normal to the main flow axis 15 of the conduit 14. The support 2 is formed and positioned in the conduit 14 such that the longitudinal channels 3 are parallel to the main flow axis 15 of the conduit 14. Therefore, the gas introduced to the conduit 14 via the fluid input 17 can flow as far as a first reactor 1. The gas passes through the support 2 of the first reactor 1 via all the parallel longitudinal channels 3, where carbon dioxide and/or carbon monoxide can be converted. FIG. 9 for example illustrates a device 16 comprising three reactors 1 arranged in series.

According to an embodiment of the invention, the supports 2 in series can extend over the entire section of the conduit 14. Therefore, the entire gas flow upstream of a reactor 1 flows through the longitudinal channels 3, and the rate of conversion of carbon monoxide and/or carbon dioxide between the upstream of said support 2 and the downstream of said support 2 is maximised.

Figure 10:
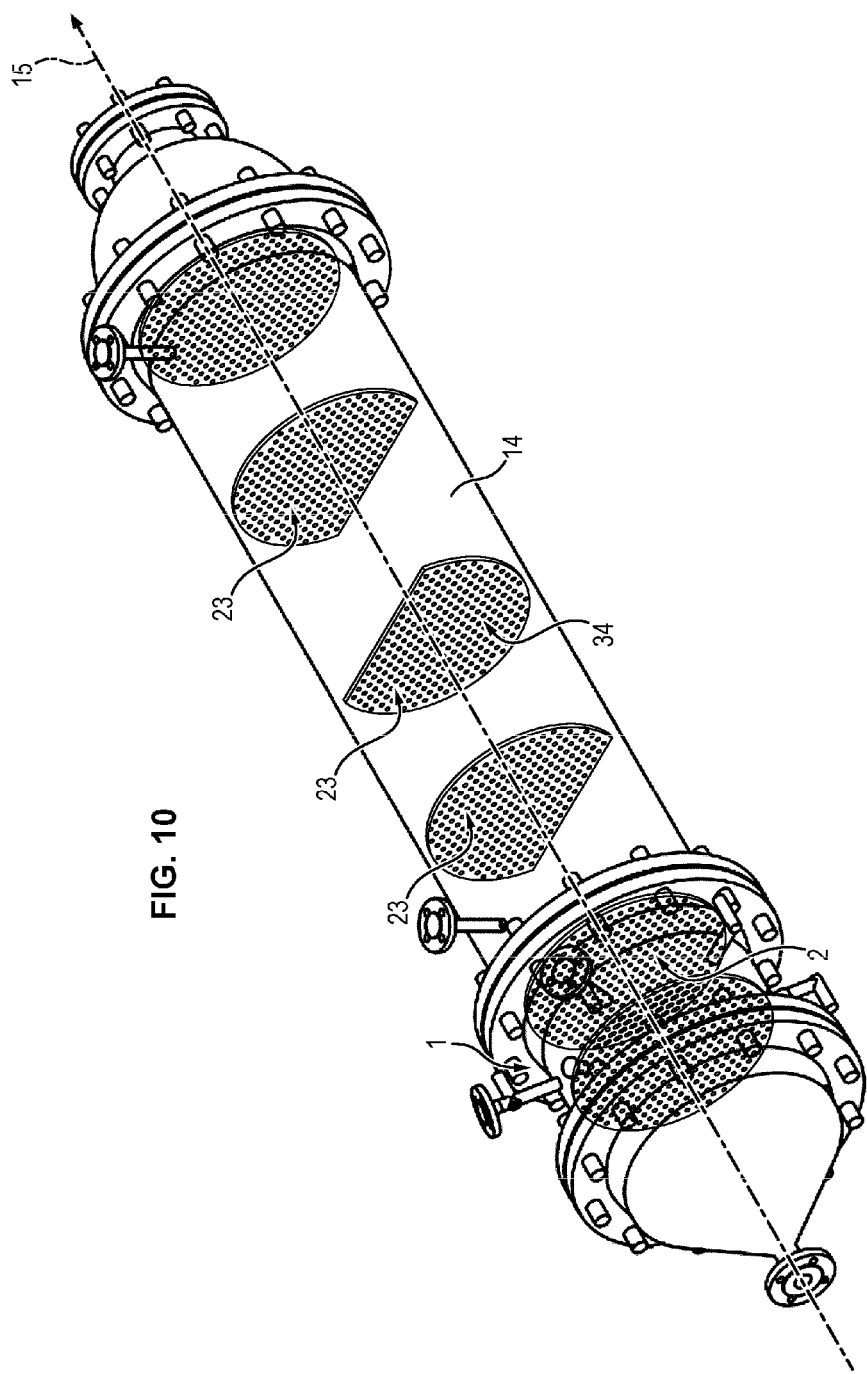

In reference to FIG. 10, a heat exchanger 34, for example of "shell and tube" type, can be arranged downstream of the reactor or reactors 1, in the conduit 14 of the device 16 or at the output of the device 16. The gaseous products coming from the reactor 1 are condensed in the heat exchanger 34, for example by contact with cooled tubes of the heat exchanger, by a heat transfer fluid circulating between the chicanes 23 at a temperature between 20 and 40° C., for example around 30° C. The heat exchanger 34 is configured to cool the gas at output from the reactor 1. The heat exchanger 34 is configured to cool a gas flow having a rate greater than 50 m$^3$/h, especially greater than 100 m$^3$/h, and more preferably greater than 300 m$^3$/h. The heat exchanger 34 is configured for example to cool a gas methane flow having a rate greater than 50 m$^3$/h. The heat exchanger 34 is also configured to cool a gas flow comprising $CO_2$ and dihydrogen, said gas flow having a rate greater than 300 m$^3$/h.

Figure 11:
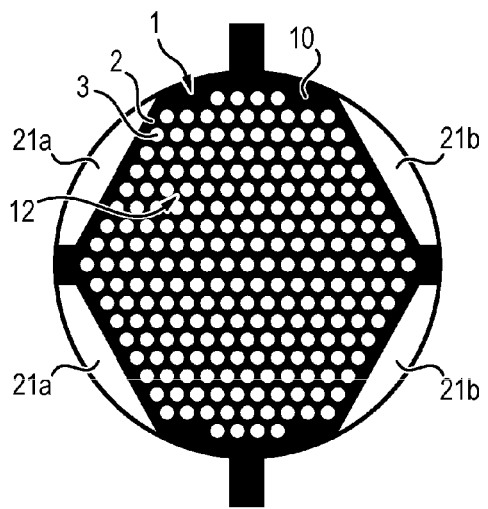
Figure 12:
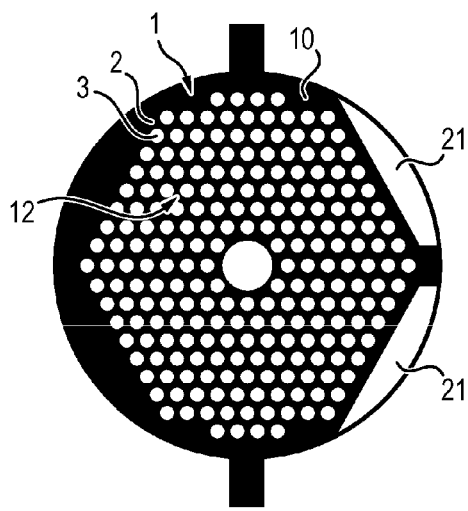
Figure 13:
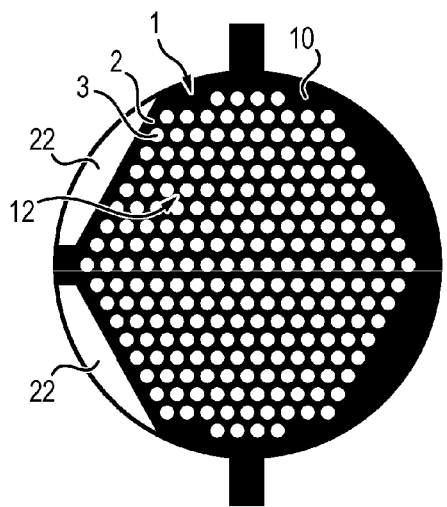

In reference to FIG. 11, FIG. 12 and FIG. 13, the support 2 can extend over part of the section of the conduit 14 only. The section of the conduit 14 also comprises a perforated part 21, via which gas can escape. This perforated part 21 exhibits hydrodynamic resistance lower than the rest of the support 2: the flow is favoured there. Several supports 2 can be arranged in series, the perforated parts 21 of the supports 2 being misaligned relative to the main flow axis 15 of the conduit 14. Therefore, mixing of the gases comprising carbon dioxide and/or carbon monoxide to be converted is favoured. At the same time a conduit 14 can also comprise supports 2 extending over the entire section of the conduit 14 and supports 2 forming perforated parts 21 of the section. The reactor 1 can comprise three supports 2, for example each of the supports 2 being illustrated respectively in FIG. 11, FIG. 12 and FIG. 13. Each support 2 forms a perforated part 21 of the section into which said support 2 extends. The perforated parts 21 are not aligned between each of the supports 2.

FIG. 11 schematically illustrates a support 2 adapted to form four perforated parts 21a and 21b when the support 2 is inserted into the conduit 14. FIG. 12 schematically illustrates a support 2 adapted to form three perforated parts 21 and 22 when the support 2 is inserted into the conduit 14. FIG. 13 schematically illustrates a support 2 adapted to form two perforated parts 22 when the support 2 is inserted into the conduit 14. The supports 2 of FIG. 11, FIG. 12 and FIG. 13 can be mounted in series so that the gas containing $CO_2$ and/or CO passes through a reactor 1 once only. At the input of the support 2 of FIG. 11, the gas can either enter the reactor 1 via the inputs of the longitudinal channels 3 and then pass through the perforated parts 22 of FIGS. 12 and 13 after the conversion reaction, or enter via the perforated parts 21a and 21b. The gas containing $CO_2$ and/or CO entering via the perforated parts 21a can then be directed to the longitudinal channels 3 of the support 2 of FIG. 12 to exit via the perforated part 22 of FIG. 13 after the conversion reaction. The gas comprising $CO_2$ and CO entering via the perforated parts 21b can be directed to the perforated part 21 of FIG. 12 and then to the longitudinal channels 3 of FIG. 13.

Figure 14:
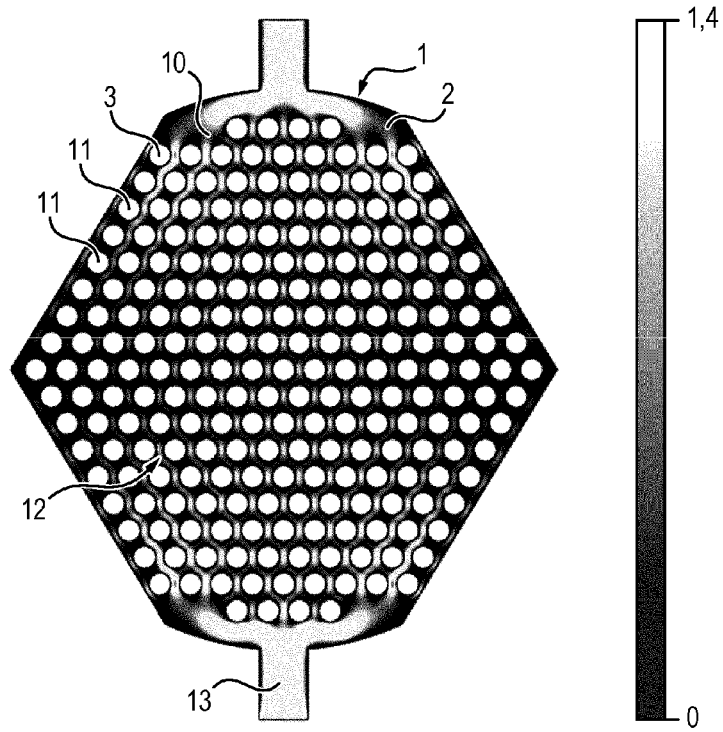
FIG. 14 illustrates a digital simulation of the local speed of a flow of heat transfer fluid in a flow channel according to a preferred embodiment of the invention.
Figure 15:
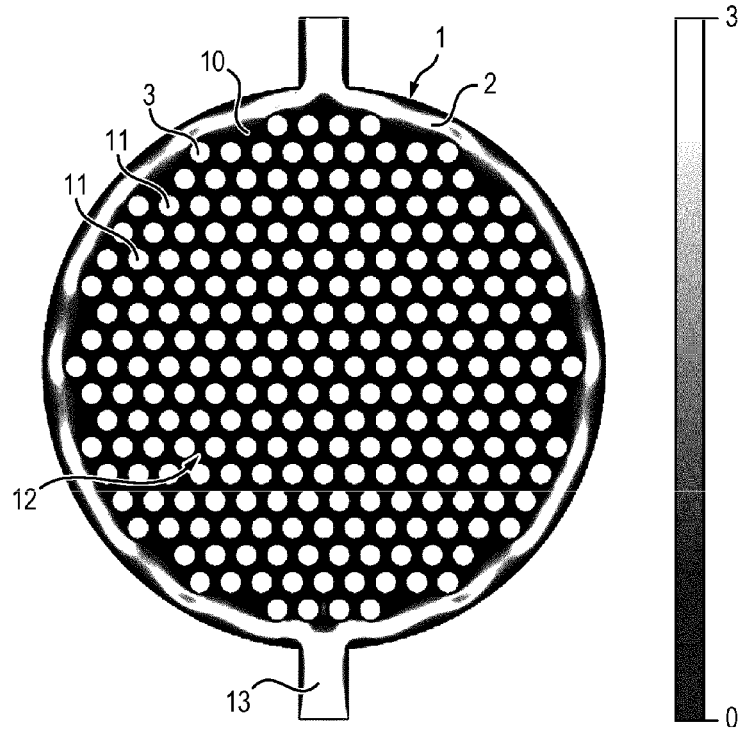
FIG. 15 illustrates a digital simulation of the local speed of a flow of heat transfer fluid in a flow channel according to an embodiment of the invention.

In reference to FIG. 14, FIG. 15, FIG. 16 and FIG. 17, the obstacles 11 of the support 2 can be arranged in the flow channel 10 of the heat transfer fluid so as to optimise the homogeneity of the temperature in the longitudinal channels 3. FIG. 14 illustrates a digital simulation of the local speed of a flow of heat transfer fluid 13 in the flow channel 10 according to a preferred embodiment of the invention. The scale to the right of the figure corresponds to speeds in $m \cdot s^{-1}$. FIG. 15 illustrates a digital simulation of the local speed of a flow of heat transfer fluid 13 in a flow channel 10 according to an embodiment of the invention. The scale to the right of the figure corresponds to speeds in $m \cdot s^{-1}$. The disparities in local flow speeds are greater in the embodiment illustrated in FIG. 15 than in FIG. 14. In fact, the geometry of the flow channel causes hydrodynamic resistance which is lower at the periphery of the flow channel 10. The flow speeds of the heat transfer fluid 13 are higher at the periphery than in the rest of the flow channel 10. This configuration is unfavourable for optimising the homogeneity of the temperature in the longitudinal channels 3. Preferably, the network 12 has a mesh defining a mesh surface and the form of the support 2 is adapted so that the average speed of the heat transfer fluid 13 in flow measured on a mesh surface in a plane parallel to the plane of the network 12 and centred on an axis of revolution of a first cylinder is between 0.5 and 1.5 times the average speed of the heat transfer fluid 13 on a mesh surface in a plane parallel to the plane of the network 12 and centred on an axis of revolution 7 of a second cylinder adjacent to the first cylinder. Therefore, the temperature in the longitudinal channels can be controlled uniformly.

Figure 16:
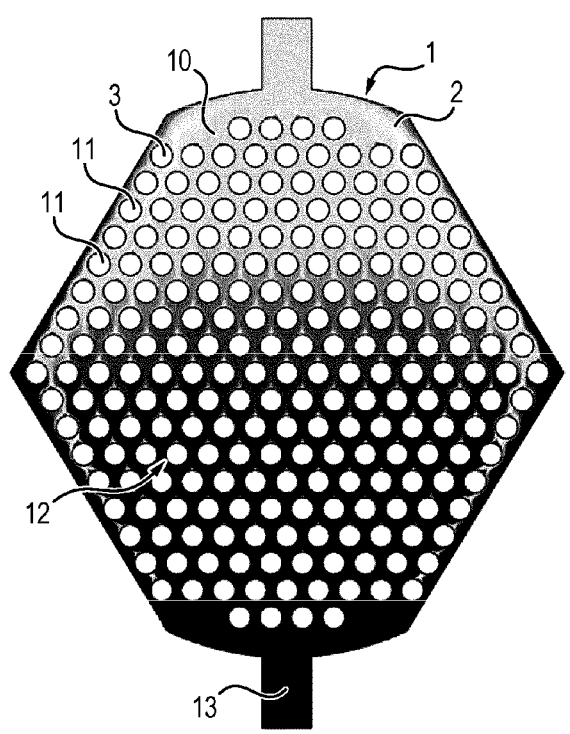
FIG. 16 illustrates a digital simulation of the local temperature of a flow of heat transfer fluid in a flow channel according to a preferred embodiment of the invention.
Figure 17:
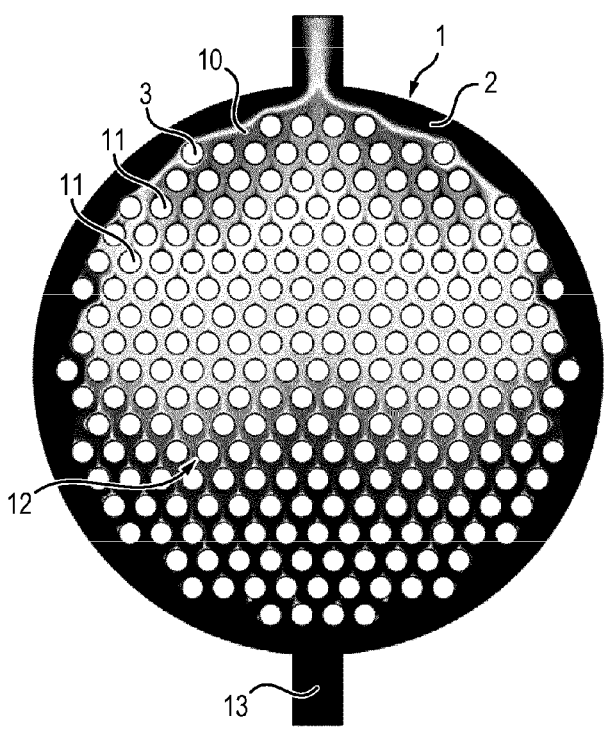
FIG. 17 illustrates a digital simulation of the local temperature of a flow of heat transfer fluid in a flow channel according to an embodiment of the invention, FIG. 18 schematically illustrates a process for conversion of carbon dioxide and/or carbon monoxide according to an embodiment of the invention, FIG. 19 schematically illustrates the use of a device according to an embodiment of the invention in a system comprising a source of carbon dioxide, FIG. 20 schematically illustrates a part of a reactor according to an embodiment of the invention for generating plasma in DBD, FIG. 21 schematically illustrates a part of a reactor according to an embodiment of the invention for generating plasma in DBD, FIG. 22 schematically illustrates a part of a reactor according to an embodiment of the invention, for generating pulsed plasma.

FIG. 16 illustrates a digital simulation of the local temperature in a flow of heat transfer fluid 13 in a flow channel according to a preferred embodiment of the invention. FIG. 17 illustrates a digital simulation of the local temperature in a flow of heat transfer fluid in a flow channel according to an embodiment of the invention. The geometry of the flow channel 10 illustrated in FIG. 16 controls the temperature of the longitudinal channels 3 more uniformly. In fact, to maximise the effectiveness of the conversion reaction of $CO_2$ and/or CO, it is preferable to maintain the temperature between 250° C. and 300° C. and therefore control the cooling of the reactor 1, since the conversion reaction is exothermal.

Executing Conversion of Carbon Dioxide and/or Carbon Monoxide

Figure 18:
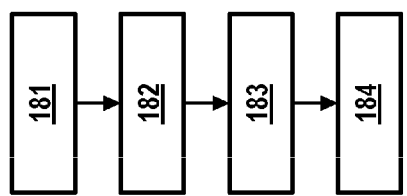

In reference to FIG. 18, a process for conversion of carbon dioxide and/or carbon monoxide comprises the steps of:
  providing 181 of a reactor 1,
  injection 182 of a gas comprising carbon dioxide and/or carbon monoxide and dihydrogen into the longitudinal channel or longitudinal channels 3 of the reactor 1, and
  application 184 of an electrical potential between the support 2, acting as cathode, and the electrode or wire electrodes 4 acting as anode, the potential being adapted to generate plasma in the volume of the longitudinal channel or longitudinal channels 3 in between the wire electrode 4 and the wall or walls of each longitudinal channel 3.

Preferably, the conversion of carbon dioxide and/or carbon monoxide comprises also a step 183 for control of the temperature of the reactor 1 between 150° C. and 300° C., and preferably between 250° C. and 300° C. The yield for conversion of carbon dioxide and/or carbon monoxide of hydrocarbon and or alcohol during hydrogenation reaction is maximal in a temperature range between 250° C. and 300° C. Below this temperature, the conversion of carbon dioxide causes production of unwanted secondary products, for example nickel tetracarbonyl if the catalyst 6 includes nickel. Above 300° C., the conversion of carbon dioxide causes production of carbon monoxide. Control of the temperature can be ensured by injection of the heat transfer fluid 13 into the flow channel 10 formed by the support 2. Since the conversion reaction of carbon dioxide and/or carbon monoxide of hydrocarbon and or alcohol is exothermal, the heat transfer fluid 13 can be cooled outside the flow channel 10 and its temperature controlled by a thermostat. Preferably, the process can be used to produce heat. The process is preferably executed at atmospheric pressure.

During application 184 of an electrical potential, the applied electrical potential is preferably an alternative potential, such as a pulsed or sinusoidal potential. The applied electrical potential preferably has an amplitude between 5 kV and 50 kV, especially between 10 kV and 20 kV. Finally, the electrical potential applied preferably has a frequency between 0.5 MHz and 100 MHz, and especially between 1 MHz and 20 MHz. These characteristics of the applied electrical potential, taken independently or combined, favour the appearance of active sites on the surface of the catalyst 6 and increase the conversion rate. According to the molar ratio between $CO_2$ and Hz, the formation of a given hydrocarbon and/or of a given alcohol can be preferred. For example, with a molar ratio of 1 $CO_2$ to 4 $H_2$, methane ($CH_4$) is preferably formed. The process is preferably used to produce hydrocarbon and more particularly methane.

Figure 19:
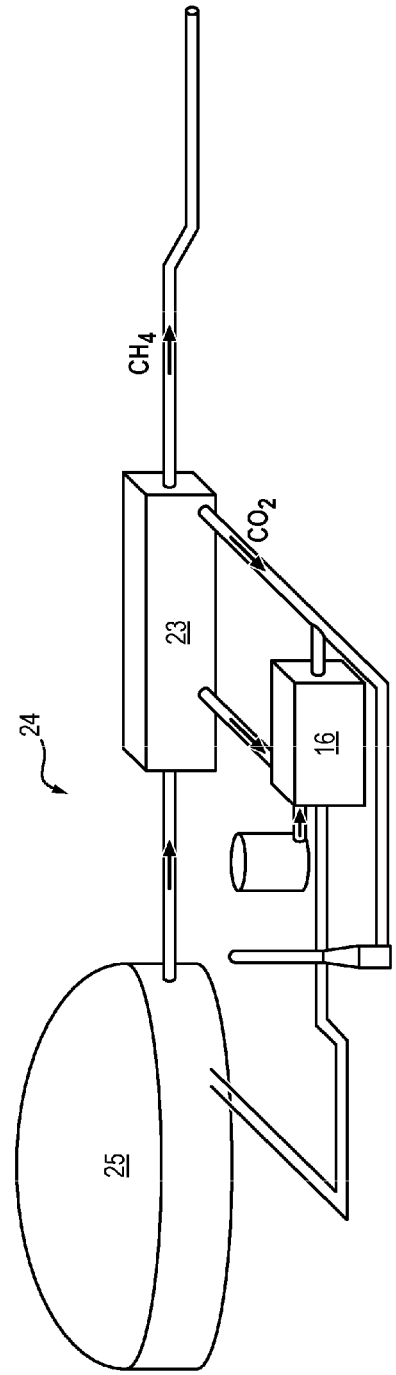

In reference to FIG. 19, a methaniser 24 (common on farms, for example) can advantageously comprise a device 16 according to an embodiment of the invention. The methaniser comprises a digester 25. The digester 25 is a reactor adapted to anaerobic fermentation of organic matter. The digester 25 emits raw biogas to a biogas processing unit 23. The biogas processing unit 23 is adapted to separate biomethane from the other gaseous compound of the raw biogas emitted by the digester 25. The biogas processing unit 23 comprises a biomethane output connected for example to the gas network. The biogas processing unit 23 comprises another output sending carbon dioxide to the device 16. Dihydrogen, coming from the hydrolysis of water for example, is also sent to the device 16 to allow the conversion reaction. After conversion of carbon dioxide by the device 16, the device 16 puts out water and methane which is injected back into the biogas processing unit 23. Therefore, the production rate of methane from the methaniser 24 is maximised, and carbon dioxide emissions into the atmosphere are minimised. Preferably, a condenser is connected to the fluid output 18 of the device 16. The condenser is adapted to condense at least one element from water and hydrocarbon.

Examples

A reactor 1 comprising three longitudinal channels 3 was tested. The longitudinal channels 3 can be utilised to generate plasma in DBD (Dielectric Barrier Discharge) or pulsed plasma.

The Device for Generating Plasma in DBD

Figure 20:
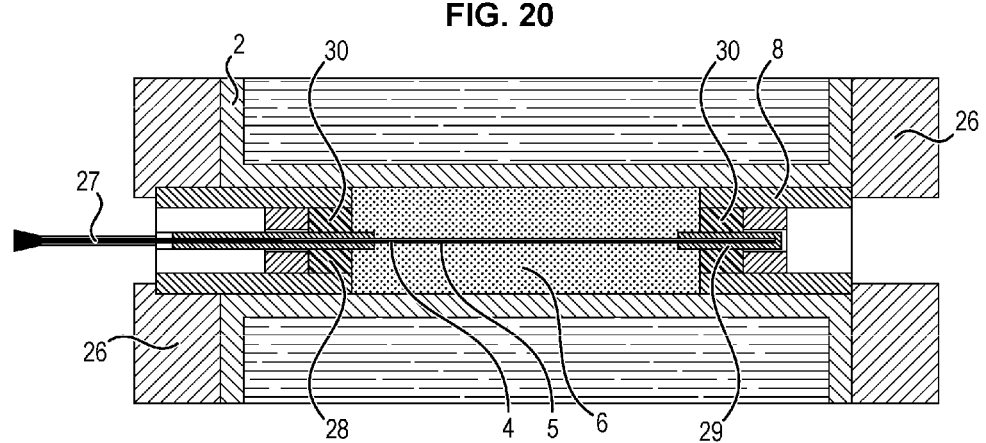

In reference to FIG. 20, setting up a reactor 1 starts with fixing a second lower support 26 onto the external surface of the support 2. The cylindrical retaining part of the stopper 8 is then placed in the cell stopped against the second support 26. The electrode 4 comprises a stripped high-voltage cable 27. The high-voltage cable 27 is introduced to a tube of dielectric material made of alumina forming an electrically insulating layer 5. A retaining sleeve 28 is slid along the electrode which is also introduced into a lower sleeve 29. The sintered glass part 30 is placed around the lower sleeve 29 which is introduced to the crucible of the second lower support 26. The catalyst 6 is then poured around the electrode via the upper part of the longitudinal channel 3. Another sintered glass part 30, as well as the second upper support 26, are slid into the retaining sleeve 28 as far as the catalyst 6. A cable and sleeve wedge is placed on the second support 26. Finally the second upper support 26 is fixed to the outer surface of the support 2.

Figure 21:
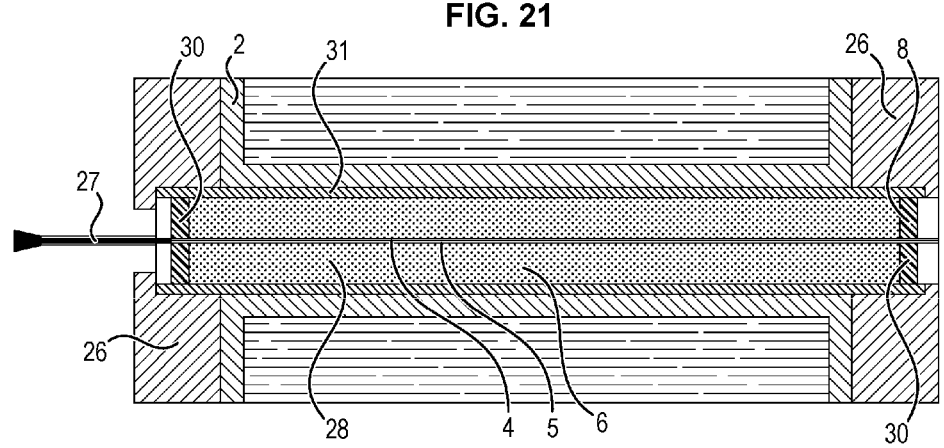

In reference to FIG. 21, and according to a preferred embodiment of the invention, a layer of dielectric material 31 can be arranged between the catalyst 6 and the support 2. The layer of dielectric material 31 can for example be constituted by a cylindrical tube made of dielectric material 31 inserted into the longitudinal channel 3, into which the wire electrode 4 is inserted, preferably covered by an electrically insulating layer 5 and by the catalyst 6. The wire electrode 4 can also be inserted into a sheath made of dielectric material, the sheath made of dielectric material being covered by the catalyst 6. A screen is placed between the support 2 and the cylindrical tube made of dielectric material 31 to hold the catalyst 6. The geometry of the cylindrical tube made of dielectric material 31 is adapted to receive the catalyst 6 over a length according to the main flow axis 15 greater than the length of the longitudinal tube 3 formed by the support 2. Preferably, the reactor 1 comprises the catalyst 6 upstream of the longitudinal channel 3 over a length greater than 0.5 cm, and especially greater than 1 cm. Preferably, the reactor 1 comprises the catalyst 6 downstream of the longitudinal channel 3 over a length greater than 0.5 cm, and especially greater than 1 cm. Therefore, this avoids the formation of preferred electrical paths potentially ending up with formation of an electrical arc. In fact, in other embodiments, the junction between the catalyst 6 and the stopper 8 can favour the appearance of preferred electrical paths. Due to the geometry of the cylindrical tube made of dielectric material, this junction is away from the longitudinal channel 3 formed by the support 2.

The Device for Generating Pulsed Plasma

Figure 22:
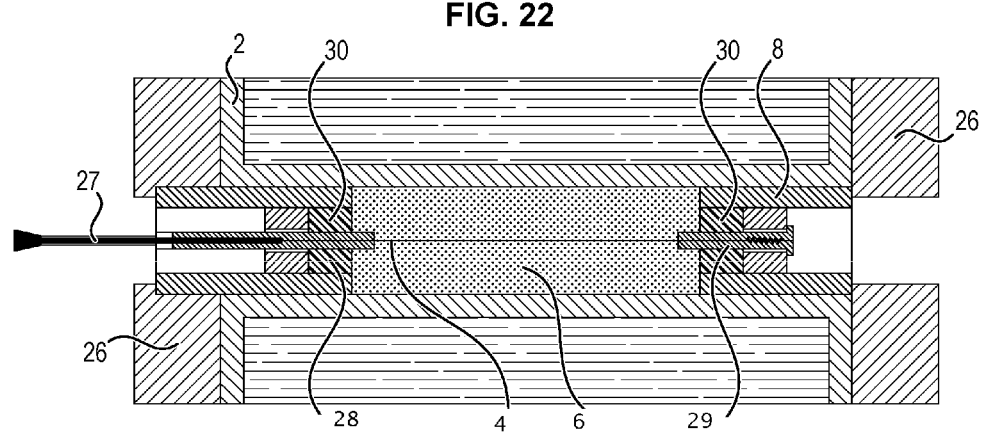

In reference to FIG. 22, the wire electrode 4 is not inserted into a rigid dielectric tube. It is therefore necessary to tension the electrical cable between two fixed points. Setting up the cell starts with fixing the second lower support 26 onto the outer surface of the support 2. The cylindrical part of the stopper 8 is then placed in the cell stopped against the second lower support 26. An upper retaining sleeve 28 is slid along the high-voltage cable 27. The cable is then introduced into the lower sleeve 29 which can be opened into two for introduction and fixing of the electrical cable. The lower sleeve 29 is then closed and fixed to the cylindrical part of the stopper via a self-fastening seal made of polymer. The sintered glass part 30, in the form of a ring, is placed around the lower sleeve 29 which is introduced to the crucible of the cylindrical part of the stopper 8. The catalyst 6 is then poured around the electrode via the upper part of the longitudinal channel 3. Another sintered glass part, as well as the cylindrical part of the stopper 8 are slid into the upper sleeve 28 as far as the catalyst 6. The high-voltage cable is then tensed, a cable and sleeve wedge containing a sheath jaw and a self-fastening seal for retaining tension in the cable is placed on the cylindrical part of the stopper. Finally the second upper support 26 is fixed onto the outer surface of the support 2.

Conversion $CO_2$ conversion reaction of hydrocarbon by dihydrogen is exothermal. For production of methane, the best yield is obtained for a reactor temperature 1 of between 250° C. and 300° C. The heat transfer fluid 13, in this case oil, is preheated to 200° C. by a heating resistor. A pump is started up so as to have the oil circulate in a loop in the flow channel 10. $CO_2$ and dihydrogen are then sent to the reactor 1. The $CO_2$ and dihydrogen ratio is kept constant. The ratio between the quantity of $CO_2$ injected in gaseous form into the reactor 1 and the quantity of dihydrogen injected in gaseous form into the reactor 1 is preferably between 0.20 and 0.30 and especially substantially equal to a quarter. Therefore, the production of methane is favoured before the production of other possible reaction products. If CO is utilised in place of $CO_2$, the ratio between the quantity of CO injected in gaseous form into the reactor 1 and the quantity of dihydrogen injected in gaseous form into the reactor 1 is preferably between 0.25 and 0.40 and especially substantially equal to a third. Therefore, the production of methane is also favoured before the production of other possible reaction products.

An electrical potential generator connected to the anode and the cathode is powered up at a frequency of 72 kHz. The voltage is controlled between 15 and 25 kV. A separator balloon is connected fluidically to the fluid output 18 of the conduit 14. The balloon can be cooled. The production of hydrocarbon is measured by collecting and analysing gas and liquid obtained at output of the conduit 14. The rate of the oil pump is adjusted continuously as a function of the temperature of gases at output of the reactor 1 and of the temperature of the return oil.

After measuring, the gaseous phase at output of the conduit 14 comprises 50% methane, 12.5% $CO_2$, and 37.5% dihydrogen. The liquid phase at output of the conduit 14 comprises 100% water, after measuring.

Therefore, the reactor 1 can enable the capture and storage of $CO_2$, for example put out industrially by a cement plant or steel mill.

The process for conversion of carbon dioxide and/or carbon monoxide according to an embodiment of the invention can for example treat the products of pyrogasification of wood waste. In fact, after pyrolysis and gasification pyrogasification of wood mainly produces $CO_2$, CO and $H_2$. It is therefore possible to produce hydrocarbon, such as methane, via a process according to an embodiment of the invention.

REFERENCES

[1] Gao, J., Wang, Y., Ping, Y., Hu, D., Xu, G., Gu, F., & Su, F. (2012). A thermodynamic analysis of methanation reactions of carbon oxides for the production of synthetic natural gas. *RSC Advances*, 2(6), 2358-2368.
[2] E&E Consultant, Hespul, S. (2014). *Study of hydrogen and methanation as a process for validating surplus electricity*. E&E Consultant, Hespul, Solagro: Cassel, France.
[3] Ocampo, F., Louis, B., & Roger, A. C. (2009). Methanation of carbon dioxide over nickel-based CeO. 72ZrO. 28O2 mixed oxide catalysts prepared by sol-gel method. *Applied Catalysis A: General*, 369(1-2), 90-96.
[4] Hoeben, W. F. L. M., van Heesch, E. J. M., Beckers, F. J. C. M., Boekhoven, W., & Pemen, A. J. M. (2015). Plasma-Driven Water-Assisted $CO_2$ Methanation. *IEEE Transactions on Plasma Science*, 43(6), 1954-1958.

The invention claimed is:

1. A reactor for conversion of carbon dioxide or carbon monoxide into hydrocarbon and/or alcohol, comprising:
a support made of an electrically and thermally conductive material, the support forming a wall of a longitudinal channel, the longitudinal channel passing through the support, the support acting as a cathode of the reactor,
a wire electrode forming an anode of the reactor, the wire electrode comprising a part that extends within the longitudinal channel along the longitudinal channel, the part being arranged at a distance from the wall of the longitudinal channel, the part being optionally covered by an electrically insulating layer,
a catalyst configured to catalyse a conversion reaction of carbon dioxide or carbon monoxide into hydrocarbon and/or alcohol, the catalyst being located between the wire electrode and the wall of the longitudinal channel,
wherein the longitudinal channel is a plurality of longitudinal channels, the plurality of longitudinal channels being arranged according to a bidimensional network according to a plane of the network, the plurality of longitudinal channels being parallel to each other and perpendicular to a plane of the network.

2. The reactor according to claim 1, wherein the longitudinal channel is a cylinder of revolution, and wherein the wire electrode is positioned along an axis of revolution of the cylinder of revolution.

3. The reactor according to claim 1, wherein the longitudinal channel comprises two ends, each end is fitted with a stopper made of an electrically insulating material, each stopper being permeable to gas and having each a through passage into which the wire electrode is inserted.

4. The reactor according to claim 1, wherein the electrically and thermally conductive material of the support is a metal.

5. The reactor according to claim 1, wherein the longitudinal channel has a diameter of less than 2 cm, and wherein a length of the channel is less than 20 cm.

6. The reactor according to claim 1, wherein the catalyst comprises at least one element selected from cerium dioxide, mesoporous cerium dioxide, nickel, zirconium dioxide, hydrotalcite, clay and their mixtures.

7. The reactor according to claim 1, wherein the support further forms:

a flow channel of a heat transfer fluid, and
an obstacle in the flow channel of the heat transfer fluid-, the obstacle comprising the longitudinal channel, the flow channel of the heat transfer fluid and the longitudinal channel being separated by the support.

8. The reactor according to claim 7, wherein the bidimensional network has a mesh defining a mesh surface,
wherein the heat transfer fluid in flow has a first average speed measured on the mesh surface in a plane parallel to the plane of the network and centred on an axis of revolution of a first cylinder,
wherein the heat transfer fluid in flow has a second average speed measured on the mesh surface in a plane parallel to the plane of the network and centred on an axis of revolution of a second cylinder adjacent to the first cylinder,
wherein the support has a form configured so that the first average speed is between 0.5 and 1.5 times the second average speed.

9. A device for conversion of carbon dioxide or carbon monoxide into hydrocarbon and/or alcohol, comprising a conduit extending along a main flow axis, the conduit comprising a plurality of reactors according to claim 7, positioned along at least a part of the conduit, each support of each reactor extending in a plane perpendicular to the main flow axis such that the longitudinal channels of the support are parallel to the main flow axis.

10. The device according to claim 9, wherein the conduit has a fluid input and a fluid output, the device further comprising:
a gas diffuser comprising carbon dioxide or carbon monoxide and hydrogen, connected to the fluid input, and
at least one condenser, connected to the fluid output and configured to condense at least one element from water and a hydrocarbon.

11. A process for conversion of carbon dioxide and/or carbon monoxide, comprising the steps of:
(a) providing a reactor according to claim 1,
(b) injecting a gas comprising carbon dioxide or carbon monoxide and dihydrogen into the longitudinal channel of the reactor,
(c) applying an electrical potential between the support acting as cathode and the wire electrode acting as anode, the electrical potential being configured to generate plasma in a volume of the longitudinal channel in between the wire electrode and the wall of the longitudinal channel.

12. The process according to claim 11, further comprising a step (d) of controlling a temperature inside the reactor, the temperature being between 150° C. and 300° C.

13. The process according to claim 11, wherein the electrical potential applied in step (c) has a frequency of between 1 MHz and 20 MHz.

14. The reactor according to claim 4, wherein the electrically and thermally conductive material of the support is steel.

15. The reactor according to claim 14, wherein the electrically and thermally conductive material of the support is stainless steel.

16. The reactor according to claim 5, wherein the longitudinal channel has a diameter of less than 1 cm, and wherein a length of the channel is less than 5 cm.

17. The reactor according to claim 7, wherein the obstacle is a pillar.

18. The reactor according to claim 7, wherein the bidimensional network is an hexagonal network.

19. The process according to claim 12, wherein the temperature inside the reactor is between 250° C. and 300° C.

* * * * *